US009844509B2

(12) United States Patent
Dewitt (10) Patent No.: US 9,844,509 B2
(45) Date of Patent: *Dec. 19, 2017

(54) HIGH THROUGHPUT FABRICATION OF NANOPARTICLES

(71) Applicant: PFIZER INC., New York, NY (US)

(72) Inventor: David M. Dewitt, Allston, MA (US)

(73) Assignee: PFIZER INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/173,752

(22) Filed: Jun. 6, 2016

(65) Prior Publication Data

US 2016/0279065 A1    Sep. 29, 2016

Related U.S. Application Data (63) Continuation of application No. 14/499,599, filed on Sep. 29, 2014, now Pat. No. 9,358,215, which is a continuation of application No. 13/716,275, filed on Dec. 17, 2012, now Pat. No. 8,846,077, which is a continuation of application No. 12/557,065, filed on Sep. 10, 2009, now abandoned.

(60) Provisional application No. 61/095,724, filed on Sep. 10, 2008.

(51) Int. Cl.
| | |
|---|---|
| *A61K 9/51* | (2006.01) |
| *A61K 9/16* | (2006.01) |
| *A61K 47/48* | (2006.01) |
| *B82Y 5/00* | (2011.01) |
| *A61J 3/00* | (2006.01) |
| *A61K 31/337* | (2006.01) |

(52) U.S. Cl.
CPC .............. *A61K 9/1682* (2013.01); *A61J 3/00* (2013.01); *A61K 9/5123* (2013.01); *A61K 9/5146* (2013.01); *A61K 9/5192* (2013.01); *A61K 31/337* (2013.01); *A61K 47/48969* (2013.01); *B82Y 5/00* (2013.01); *A61K 9/5153* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 5,654,008 A | 8/1997 | Herbert et al. | |
| 5,849,783 A | 12/1998 | Egyud | |
| 5,869,103 A | 2/1999 | Yeh et al. | |
| 6,291,013 B1 | 9/2001 | Gibson et al. | |
| 6,485,690 B1 | 11/2002 | Pfost et al. | |
| 6,551,619 B1 | 4/2003 | Penkler et al. | |
| 8,846,077 B2 * | 9/2014 | Dewitt ................. | A61K 9/5146 424/449 |
| 9,358,215 B2 * | 6/2016 | Dewitt ................. | A61K 9/5146 |

(Continued)

OTHER PUBLICATIONS

E.M.M.D. Valle. "Cyclodextrins and Their Uses: A Review." Process Biochemistry, vol. 39, 2004, pp. 1033-1046.*

(Continued)

*Primary Examiner* — Isaac Shomer
(74) *Attorney, Agent, or Firm* — Saliwanchik, Lloyd & Eisenschenk (57) ABSTRACT

This application provides a high throughput method of making nanoparticles that utilizes plates comprising wells (e.g., 96-well plates).

2 Claims, 1 Drawing Sheet

(56) References Cited

U.S. PATENT DOCUMENTS

| | | |
|---|---|---|
| 2002/0099051 A1 | 7/2002 | Fidler et al. |
| 2003/0211164 A1 | 11/2003 | Wright et al. |
| 2004/0247680 A1 | 12/2004 | Farokhzad et al. |
| 2004/0248778 A1 | 12/2004 | Gloger et al. |
| 2005/0142206 A1 | 6/2005 | Brown et al. |
| 2005/0276859 A1* | 12/2005 | Rickey ............... A61K 9/1647 424/489 |
| 2007/0098802 A1 | 5/2007 | Farr et al. |

OTHER PUBLICATIONS

Avgoustakis, K. "Pegylated Poly(Lactide) and Poly(Lactide-Co-Glycolide) Nanoparticles: Preparation, Properties and Possible Applications in Drug Delivery" *Current Drug Delivery*, 2004, pp. 321-333, vol. 1, No. 4.

Ressing, M. E. et al. "The Influence of Sucrose, Dextran, and Hydroxypropyl-β-cyclodextrin as Lyoprotectants for a Freeze-Dried Mouse IgG$_{2a}$ Monoclonal Antibody (MN12)" *Pharmaceutical Research*, 1992, pp. 266-270, vol. 9, No. 2.

Gref, R. et al. "The controlled intravenous delivery of drugs using PEG-coated sterically stabilized nanospheres" *Advanced Drug Delivery Reviews*, 1995, pp. 215-233, vol. 16.

Martin Del Valle, E. M. "Cyclodextrins and their uses: a review" *Process Biochemistry*, 2004, pp. 1033-1046, vol. 39.

Farokhzad, O. C. et al. "Nanoparticle-aptamer bioconjugates for cancer targeting" *Expert Opin. Drug Deliv.*, 2006, pp. 311-324, vol. 3, No. 3.

Theriault, R. et al. "Phase I clinical evaluation of [SP-4-3(R)]-[1,1-cyclo-butanedicarboxylato(2−) ](2-methyl-1,4-butanediamine-N,N$^1$) platinum in patients with metastatic solid tumors" *Cancer Chemother Pharmacol*, 1993, pp. 333-337, vol. 31.

* cited by examiner

HIGH THROUGHPUT FABRICATION OF NANOPARTICLES

CROSS-REFERENCE TO RELATED APPLICATIONS

This application is a continuation of U.S. Ser. No. 14/499,599, filed Sep. 29, 2014, now U.S. Pat. No. 9,358,215, which is a continuation of U.S. Ser. No. 13/716,275, filed Dec. 17, 2012, now U.S. Pat. No. 8,846,077, which is a continuation of U.S. Ser. No. 12/557,065, filed Sep. 10, 2009, now abandoned, which claims the benefit of U.S. Provisional Application Ser. No. 61/095,724, filed Sep. 10, 2008, the disclosures of which are hereby incorporated by reference in their entirety, including all figures, tables and amino acid or nucleic acid sequences.

This invention was made with United States Government support under Cooperative Agreement Number 70NANB7H7021 awarded by the National Institute of Standard and Technology (NIST). The United States Government has certain rights in the invention.

BRIEF SUMMARY OF THE INVENTION

This application provides a high throughput method of making nanoparticles that utilizes plates comprising wells (e.g., 96-well plates).

DETAILED DISCLOSURE OF THE INVENTION

Figure 1:
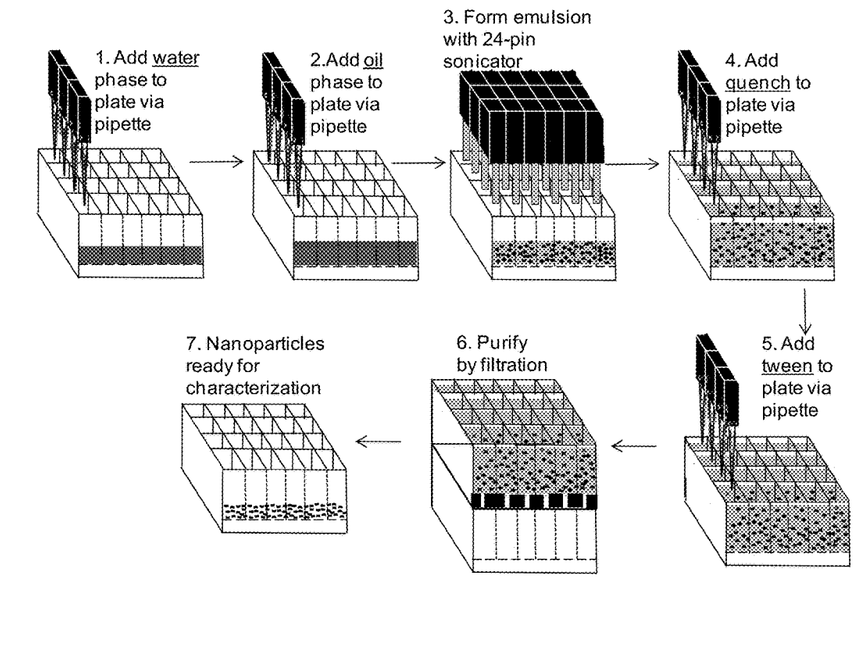
FIG. 1—Illustration of high throughput process.

This application provides a high throughput method of making nanoparticles that utilizes plates comprising wells (e.g., 96-well plates). In this aspect of the invention, stock solutions can be made which comprise:

a) a first stock solution comprising an oil phase which contains drug and polymers admixed with organic solvents;

b) a second stock solution comprising a surfactant and solvents (typically an aqueous phase);

c) a third stock solution comprising a water or buffer quench; and d) a fourth phase comprising a drug solubilizer.

In one aspect of the invention, an aqueous phase is first pipetted by hand or via a fluid handling robot into a standard multi-well polypropylene plate (e.g., 250 uL is pipetted into a 96 well polypropylene plate). A stock solution comprising an oil phase can then be pipetted into the aqueous phase already present in the plate by hand or robot. The preferred water:oil ratio is 5:1 but ranges from 1:1 to 1:15 will also form emulsions and can be used in this aspect of the invention. In certain embodiments, the stock solution comprising an oil phase can be added to the plate first and the stock solution comprising an aqueous phase can be added to the solution containing the oil phase. Following the admixture of the first and second stock solutions, sonication is performed on the combined stock solutions to form an emulsion. The emulsion can then be added to a high volume (1 or 2 or 5 mL per well) multi-well plate loaded with the third stock solution comprising a water or buffer quench and cooled to 4° C. The quench solution can be, optionally, premixed with a drug solubilizer (e.g., TWEEN-80 or Hydroxypropyl-beta-cyclodextrin) or a drug solubilizer can be added to the quench solution to dissolve unencapsulated drug.

In a further aspect of the invention, the nanoparticle solution can then be transferred to a multi-well filter plate for rough filtration. For example, a 0.45 micron membrane can be used to remove large particles and drug crystals via vacuum. The filtrate can then be transferred to another filter plate with a 100 kDa molecular weight cutoff (MWCO) membrane to filter out small particles like drug micelles (fine filtration). Individual centrifuge filters can also be used if larger MWCO are required. The fine filtration is performed in a centrifuge at 4000 rpm and at 4° C. until all liquid is filtered away. The particles can then be washed by diafiltration which involves the addition of water or buffers to the filter plate and centrifugation to remove the added water or buffers. This step can be, optionally, repeated 1, 2, 3, 4, 5, or 10 times to remove any excess material including organic solvents not incorporated into the nanoparticles. After the final wash, the nanoparticles can be resuspended in water or an aqueous solution, frozen using liquid nitrogen or lyophilized for future use.

First Stock Solution (Active Agents and Polymers)

As discussed above, a first stock solution comprising an organic phase which contains drug and polymers admixed with organic solvents is provided. Thus, the first stock solution can contain polymers comprising a targeting agent coupled to a PEG (poly(ethylene glycol)) polymer (via the α terminus) that is then coupled to biocompatible and biodegradable hydrophobic polymer (polyester) blocks. Alternatively, the polymer can comprise PEG coupled to biocompatible and biodegradable hydrophobic polymer (polyester) blocks (without a targeting agent). Exemplary polyesters suitable for use in the disclosed methods copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene inline), PEGylated poly(ethylene imine), poly(L-lactide-co-L-lysine), poly(serine ester), poly(4-hydroxy-L-proline ester), poly[a-(4-aminobutyl)-L-glycolic acid], and derivatives thereof. Yet other embodiments provide polymers that may be one or more acrylic polymers. In certain embodiments, acrylic polymers include, for example, acrylic acid and copolymers, methyl methacrylate copolymers, ethoxyethyl methacrylates, cyanoethyl methacrylate, aminoalkyl methacrylate copolymer, methacrylic acid alkylamide copolymer, poly(methyl methacrylate), aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters. In some other embodiments, polymers can be cationic polymers. In general, cationic polymers are able to condense and/or protect negatively charged strands of nucleic acids (e.g. DNA, RNA, or derivatives thereof). Amine-containing polymers such as poly(lysine) (Zauner et al., 1998, *Adv. Drug Del. Rev.*, 30:97; and Kabanov et al., 1995, *Bioconjugate Chem.*, 6:7), poly (ethylene imine) (PEI; Boussif et al, 1995, *Proc. Natl. Acad. Sci., USA,* 1995, 92:7297), and poly(amidoamine) dendrimers (Kukowska-Latallo et al., 1996, *Proc. Natl. Acad. Sci., USA,* 93:4897; Tang et al., 1996, *Bioconjugate Chem.,* 7:703; and Haensler et al., 1993, *Bioconjugate Chem.,* 4:372) are positively-charged at physiological pH, form ion pairs with nucleic acids, and mediate transfection in a variety of cell lines. In yet other embodiments, polymers can be degradable polyesters bearing cationic side chains (Putnam et al., 1999, *Macromolecules,* 32:3658; Barrera et al., 1993, *J. Am. Chem. Soc.,* 115:11010; Urn et al., 1999, *J. Am. Chem. Soc.,* 121:5633; and Zhou et al, 1990, *Macromolecules,* 23:3399). Examples of these polyesters include poly(L-lactide-co-L-lysine) (Barrera et al, 1993, *J. Am. Chem. Soc.,* 115:11010), poly(serine ester) (Zhou et al, 1990, *Macromolecules,* 23:3399), poly(4-hydroxy-L-proline ester) (Putnam et al, 1999, *Macromolecules,* 32:3658; and Lim et al, 1999, *J. Am. Chem. Soc.,* 121:5633). Poly(4-hydroxy-L-proline ester) was demonstrated to condense plasmid DNA through electrostatic interactions, and to mediate gene transfer (Putnam et al, 1999, *Macromolecules,* 32:3658; and Lim el al, 1999, *J. Am. Chem. Soc.,* 121:5633). These new polymers are less toxic than poly(lysine) and PEI, and they degrade into non-toxic metabolites. Organic solvents that can be used in the formation of this first solution include, but are not limited to, dichloromethane, ethyl acetate, benzyl alcohol, acetonitrile, chloroform, tetrahydrofuran, acetone, formamide, dimethylformamide, pyridines, dioxane, dimethysulfoxide and various combinations thereof.

In a particular embodiment, the molecular weight of the polymers of the nanoparticles of the invention are optimized. For example, the molecular weight of the polymer influences nanoparticle degradation rate (particularly when the molecular weight of a biodegradable polymer is adjusted), solubility, water uptake, and drug release kinetics (e.g. "controlled release"). As a further example, the molecular weight of the polymer can be adjusted such that the nanoparticle biodegrades in the subject being treated within a reasonable period of time (ranging from a few hours to 1-2 weeks, 3-4 weeks, 5-6 weeks, 7-8 weeks, etc.). In particular embodiments of a nanoparticle comprising a copolymer of PEG and PLGA, PEG and PLA or PEG, PLA and PLGA, the PEG has a molecular weight of 1,000-20,000, e.g., 5,000-10,000, 5,000-20,000, e.g., 10,000-20,000, PLA has a molecular weight of 5,000-100,000, e.g., 15,000-45,000, 20,000-70,000, or 20,000-50,000, and the PLGA has a molecular weight of 5,000-100,000, e.g., 15,000-45,000, 20,000-70,000, e.g., 20,000-50,000.

Active Agents

As discussed above, active agents (bioactive moieties) are included in the first stock solution. Active agents (also referred to as therapeutic agents, diagnostic agents or bioactive moieties agents) include, and are not limited to, therapeutic agents (e.g. anti-cancer agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.). Exemplary therapeutic agents to be delivered in accordance with the present invention include, but are not limited to, small molecules (e.g. cytotoxic agents), nucleic acids (e.g., siRNA, RNAi, and mircoRNA agents), proteins (e.g. antibodies), peptides, lipids, carbohydrates, hormones, metals, radioactive elements and compounds, drugs, vaccines, immunological agents, etc., and/or combinations thereof. In some embodiments, the agent to be delivered is an agent useful in the treatment of cancer (e.g., prostate cancer).

Some examples of therapeutic agents that can included in the first stock solution include, but are not limited to agents such as penicillins, aminopenicillins, penicillins in conjunction with penicillinase inhibitor and/or anti-fungal agents), cephalosporins, cephamycins and carbapenems, fluoroquinolones, tetracyclines, macrolides and aminoglycosides. Specific examples include, but are not limited to, erythromycin, bacitracin zinc, polymyxin, polymyxin B sulfates, neomycin, gentamycin, tobramycin, gramicidin, ciprofloxacin, trimethoprim, ofloxacin, levofloxacin, gatifloxacin, moxifloxacin, norfloxacin, sodium sulfacetamide, chloramphenicol, tetracycline, azithromycin, clarithyromycin, trimethoprim sulfate and bacitracin.

Yet other examples of therapeutic agents suitable for inclusion within the first stock solution are non-steroidal (NSAIDs) and steroidal anti-inflammatory agents (generally referred to as anti inflammatory agents (including both COX-1 and COX-2 inhibitors)). Examples include, but are not limited to, corticosteroids, medrysone, prednisolone, prednisolone acetate, prednisolone sodium phosphate, fluormetholone, dexamethasone, dexamethasone sodium phosphate, betamethasone, fluorometasone, antazoline, fluorometholone acetate, rimexolone, loteprednol etabonate, diclofenac (diclofenac sodium), ketorolac, ketorolac tromethamine, hydrocortisone, bromfenac, flurbiprofen, antazoline and xylometazoline.

Other therapeutic agents that can be incorporated into the first stock solution include anti-histamines, mast cell stabilizers and other anti-allergy agents. Examples include, but are not limited, cromolyn sodium, lodoxamide tromethamine, olopatadine HCl, nedocromil sodium, ketotifen fumarate, levocabastine HCL, azelastine HCL, pemirolast (pemirolast potassium), epinastine HCL, naphazoline HCL, emedastine, antazoline, pheniramine, sodium cromoglycate, N-acetyl-aspartyl glutamic acid and amlexanox.

Other non-limiting examples of potentially suitable therapeutic agents for incorporation into the first stock solution include anti-cancer agents such as 5-fluorouracil (5-FU), CPT-11, 10-hydroxy-7-ethylcamptothecin (SN38), S-I capecitabine, ftorafur, 5'deoxyflurouridine, UFT, eniluracil, deoxycytidine, 5-azacytosine, 5-azadeoxycytosine, allopurinol, 2-chloroadenosine, aminopterin, methylene-10-deazaaminopterin (MDAM), oxaplatin, picoplatin, tetraplatin, satraplatin, platinum-DACH, ormaplatin, [SP-4-3-(R)]-[1,1-cyclobutanedicarboxylato-(2-)](2 methyl-1,4-butanediamine-N,N')platinum (CI-973), and analogs thereof, 9-aminocamptothecin, 10,11-methylenedioxycamptothecin, karenitecin, 9-nitrocamptothecin, 6-[[2-(dimethylamino)ethyl]amino]-3-hydroxy-7H-indeno[2,1-c]quinolin-7-one dihydrochloride (TAS 103), L-phenylalanine mustard, ifosphamidemefosphamide, trophosphamide carmustine, epothilones A-E, tomudex, 6-mercaptopurine, 6-thioguanine, karenitecin, acyclovir, valacyclovir, ganciclovir, amantadine, rimantadine, lamivudine, zidovudine, bevacizumab, trastuzumab, rituximab, 20-epi-1α, 25 dihydroxyvitamin D3, 4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, antidorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinyl-spermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, carbetimer, carboplatin, carboxamide-amino-triazole, carboxyamidotriazole, methylgloyoxal maleimide, carmustine, earn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsarnitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, flurocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinarnide, RNAi, rogletimide, rohitukine, romurtide, roquinimex, rubiginone Bl, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride and combinations thereof.

Second Stock Solution

The second stock solution comprises an aqueous phase in combination with a surfactant and organic solvents. The majority of the second solution is water while the organic solvent improves drug encapsulation in the particles. The organic solvent should be the same as the solvent used in the first stock solution. The organic solvent should be slightly miscible in water, and in preferred embodiments less than 10% of the second solution. In certain embodiments, the solvent is a halogenated solvent such as carbon tetrachloride, chloroform, or methylene chloride. In other embodiments, the solvent is not halogenated. Exemplary non-halogenated organic solvents include ethyl acetate, diethyl ether, hexanes, tetrahyrofuran, benzene, acetonitrile, benzyl alcohol, and toluene.

Any surfactant may be used in the second stock solution. In certain embodiments, the surfactant is biocompatible. Exemplary surfactants include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid amides; sorbitan trioleate (Span 85) glycocholate; polysorbate 80 (TWEEN-80); sodium cholate, methyl cellulose; gelatin; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol) 5000-phosphatidylethanolamine; polyvinyl alcohol) (PVA); Pluronics (poloxamers or block copolymers of ethylene oxide and propylene oxide), sodium cholate, and phospholipids. In certain embodiments, the surfactant is polysorbate 80. The surfactant in the second stock solution may be a mixture of different surfactants and the concentration (v/v) of the surfactant in the second stock solution may range from 0.001% to 10%; 0.01% to 5%; or 0.1% to 2%. In certain embodiments, the concentration of the surfactant in the second stock solution is approximately 1%. In other embodiments, the concentration of the surfactant is approximately 0.1% or approximately 0.01%.

As noted above, the stock solutions can be added to multi-well plates by hand or by a fluid-handling robot. The solution may be added to multi-well plates (e.g., 24-, 48-, or 96-well plates). In certain embodiments, deep multi-well plates (that can hold 1-5 mL of solution) are used.

When the first and second stock solutions are combined, the ratio of the aqueous phase (second stock solution) added to the organic/oil phase (first stock solution; also designated as second stock solution:first stock solution) is 1:2.5, 1:5, 1:10, 1:15, 1:20, 1:25, 1:30, 1:40, 1:50, or 1:100. In certain embodiments, the ratio is approximately 1:5. After adding the first and second stock solutions together in a designated ratio, an emulsion is formed using vigorous agitation (e.g., sonication). A multi-tip probe sonicator (e.g., a 24 tip probe sonicator) may be used to form the primary emulsion. The duration of the sonication can range from 1 second to 60 seconds. In certain embodiments, the duration of the sonication is from 5-20 seconds or for a period of about 10 seconds. Sonication can be performed at room temperature or at other temperatures (e.g., 4° C.).

Third Stock Solution (Quenching Solutions)

After the emulsion is formed, it can be transferred to a second plate containing a quench solution (also referred to as "a third stock solution" herein) comprising water or a buffer. Where the quench solution is a buffer, it can comprise pharmaceutically acceptable excipients, buffers, salts, acids, bases and/or sugars (e.g., compositions comprising saline or phosphate buffered saline (PBS)). Sugars, such as sucrose, cyclodextran and natural polysaccharides can be used in the formulation of this stock solution. In certain embodiments, a pharmaceutically acceptable excipient is added as a quench solution. The transfer of the emulsion to a second multiwell plate can be performed by hand or via a fluid handling robot. In other embodiments, the quench solution can be added to the emulsion formed in a deep well plate by hand of a fluid handling robot. In certain embodiments, the ratio of the emulsion to the quench solution is 1:2, 1:3, 1:4, 1:5, 1:6, 1:7, 1:8, 1:9, 1:10, 1:15, 1:20, 1:25, 1:30, 1:40, 1:50, or 1:100. In certain embodiments, the ratio is approximately 1:8. In some embodiments, the third stock solution is held at a temperature between 0 and 4° C. and the combined solution (comprising the emulsion and the quench solution) is cooled to 0 to 4° C.

Fourth Stock Solution ("Drug Solubilizer")

The fourth stock solution can comprise water in combination with a surfactant and/or drug solubilizer. The drug solubilizer can dissolve unencapsulated drug so it can be separated from the particles by techniques like filtration or centrifugation. Any surfactant or drug solubilizer may also be used in the fourth stock solution. In certain embodiments, the surfactant/solubilizer is biocompatible. Exemplary surfactants include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid amides; sorbitan trioleate (Span 85) glycocholate; polysorbate 80 (TWEEN-80); cyclodextrins including beta-cyclodextrin, methyl cellulose; gelatin; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol) 5000-phosphatidylethanolamine; polyvinyl alcohol) (PVA); and phospholipids. In certain embodiments, the surfactant is polysorbate 80. The surfactant or solubilizer in the fourth stock solution may be a mixture of different surfactants and the concentration (v/v) in the stock solution may range from 0.001% to 50%; 5% to 30%; or 10% to 25%. The amount of drug solubilizer can be proportional to the amount of drug added to stock solution 1. The ratio of drug solubilizer to initial drug in stock solution 1 can be between 1:1 and 1:10 with the preferred range of 1:1 to 1:5.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Solution Preparation

A solution was made by mixing 94 milliliters of deionized water, 4 ml ethyl acetate, and 2 ml benzyl alcohol. Then, 2 grams of sodium cholate were added to the solution with mixing. This final solution is used as the aqueous phase and used for all formulations in this example. Tables 1 and 2 list the composition of the oil phases created for this example.

TABLE 1

16-5 PLA-PEG Oil phase solutions (amounts in grams)

| Oil phase solution | ethyl acetate | benzyl alcohol | 16-5 PLA-PEG | 22 kDa PLA | 80 kDa PLA | 25 kDa PLGA | 100 kDa PLGA | Docetaxel |
|---|---|---|---|---|---|---|---|---|
| 1 | 4.5 | 1.2 | 0.7 | n/a | n/a | n/a | n/a | 0.3 |
| 2 | 4.5 | 1.2 | 0.53 | 0.18 | n/a | n/a | n/a | 0.3 |
| 3 | 4.5 | 1.2 | 0.35 | 0.35 | n/a | n/a | n/a | 0.3 |
| 4 | 4.5 | 1.2 | 0.18 | 0.53 | n/a | n/a | n/a | 0.3 |
| 5 | 4.5 | 1.2 | 0.53 | n/a | 0.18 | n/a | n/a | 0.3 |
| 6 | 4.5 | 1.2 | 0.35 | n/a | 0.35 | n/a | n/a | 0.3 |
| 7 | 4.5 | 1.2 | 0.18 | n/a | 0.53 | n/a | n/a | 0.3 |
| 8 | 4.5 | 1.2 | 0.53 | n/a | n/a | 0.18 | n/a | 0.3 |
| 9 | 4.5 | 1.2 | 0.35 | n/a | n/a | 0.35 | n/a | 0.3 |
| 10 | 4.5 | 1.2 | 0.18 | n/a | n/a | 0.53 | n/a | 0.3 |
| 11 | 4.5 | 1.2 | 0.53 | n/a | n/a | n/a | 0.18 | 0.3 |
| 12 | 4.5 | 1.2 | 0.35 | n/a | n/a | n/a | 0.35 | 0.3 |
| 13 | 4.5 | 1.2 | 0.18 | n/a | n/a | n/a | 0.53 | 0.3 |

TABLE 2

28-5 PLA-PEG Oil phase solutions (amounts in grams)

| Oil phase solution | ethyl acetate | benzyl alcohol | 28-5 PLA-PEG | 22 kDa PLA | 80 kDa PLA | 25 kDa PLGA | 100 kDa PLGA | Docetaxel |
|---|---|---|---|---|---|---|---|---|
| 14 | 4.5 | 1.2 | 0.7 | n/a | n/a | n/a | n/a | 0.3 |
| 15 | 4.5 | 1.2 | 0.53 | 0.18 | n/a | n/a | n/a | 0.3 |
| 16 | 4.5 | 1.2 | 0.35 | 0.35 | n/a | n/a | n/a | 0.3 |
| 17 | 4.5 | 1.2 | 0.18 | 0.53 | n/a | n/a | n/a | 0.3 |
| 18 | 4.5 | 1.2 | 0.53 | n/a | 0.18 | n/a | n/a | 0.3 |
| 19 | 4.5 | 1.2 | 0.35 | n/a | 0.35 | n/a | n/a | 0.3 |
| 20 | 4.5 | 1.2 | 0.18 | n/a | 0.53 | n/a | n/a | 0.3 |
| 21 | 4.5 | 1.2 | 0.53 | n/a | n/a | 0.18 | n/a | 0.3 |
| 22 | 4.5 | 1.2 | 0.35 | n/a | n/a | 0.35 | n/a | 0.3 |
| 23 | 4.5 | 1.2 | 0.18 | n/a | n/a | 0.53 | n/a | 0.3 |
| 24 | 4.5 | 1.2 | 0.53 | n/a | n/a | n/a | 0.18 | 0.3 |
| 25 | 4.5 | 1.2 | 0.35 | n/a | n/a | n/a | 0.35 | 0.3 |
| 26 | 4.5 | 1.2 | 0.18 | n/a | n/a | n/a | 0.53 | 0.3 |

Nanoparticle Creation 250 microliters of the aqueous phase were pipetted into each tube of an array of 96 1-milliliter tubes. Then 50 microliters of oil phase was added to the aqueous phase in the tubes. For this example, there were 26 oil phases with one aqueous phase so each oil phase was used in 3 separate wells to create replicate formulations. Oil phases 1 and 14 were used in 12 wells each since they represented baseline formulations that could tie to previous experiments. The oil and water mixtures were formed into an emulsion by sonication with 3 cycles of 10 seconds at 60% amplitude. Between each sonication cycle, the emulsion was cooled to 10 C. After sonication, the emulsions were pipetted into another 96 deep well plate that contained 1500 microliters of deionized water and was cooled to 4 C on an ice bath. This step quenched the emulsion and stabilized the nanoparticles. Then 200 microliters of a solution of 50 wt % hydroxypropyl-beta-cyclodextrin in water was added to all wells and mixed with a pipette to solubilize unencapsulated drug. After mixing, the formulations were transferred, one per well, to Amicon Ultra-4 centrifuge filters with 100 kDa cutoff membrane. These filters were then placed in an Eppendorf 5804R centrifuge set to 4000 g and 4C and spun for 10 minutes. After the first spin cycle, 1 milliliter of a 5% Hydroxypropyl-beta-cyclodextrin in water solution was added to the filter and the filters spun again. This process, adding cyclodextrin solution and spinning, was repeated a total of 8 more times. After the last spin, the particles were resuspended with 1 milliliter deionized water and transferred to a Pall Acroprep 1 micron filter plate and spun in the centrifuge for 10 minutes. This completes the processing of the particles.

Nanoparticle Characterization

Particle diameter was measured by dynamic light scattering and results tabulated in Table 3. Docetaxel content of the formulations was measured by HPLC and shown in Table 4. Solids concentration of the formulations was measured by drying the suspensions and weighing the leftover solids and are shown in Table 5.

TABLE 3

Particle Diameter in nanometers

|   | 1   | 2   | 3   | 4   | 5   | 6   | 7   | 8   | 9   | 10  | 11  | 12  |
|---|-----|-----|-----|-----|-----|-----|-----|-----|-----|-----|-----|-----|
| A | 59  | 77  | 74  | 68  | 62  | 83  | 67  | 99  | 72  | 82  | 69  | 88  |
| B | 103 | 98  | 102 | 116 | 128 | 127 | 127 | 158 | 88  | 122 | 111 | 101 |
| C | 61  | 67  | 68  | 68  | 57  | 77  | 80  | 80  | 68  | 82  | 63  | 89  |
| D | 213 | 214 | 179 | 222 | 168 | 253 | 124 | 191 | 154 | 172 | 131 | 181 |
| E | 54  | 62  | 52  | 63  | 61  | 61  | 90  | 69  | 71  | 74  | 66  | 69  |
| F | 88  | 96  | 75  | 102 | 83  | 100 | 88  | 104 | 79  | 92  | 97  | 90  |
| G | 66  | 169 | 76  | 118 | 67  | 164 | 76  | 181 | 78  | 154 | 77  | 158 |
| H | 267 | 229 | 273 | 255 | 276 | 225 | 243 | 233 | 260 | 228 | 267 | 244 |

TABLE 4

Docetaxel Content in micrograms per milliliter

|   | 1   | 2   | 3   | 4   | 5   | 6   | 7   | 8   | 9   | 10  | 11  | 12  |
|---|-----|-----|-----|-----|-----|-----|-----|-----|-----|-----|-----|-----|
| A | 186 | 153 | 270 | 314 | 301 | 248 | 169 | 66  | 150 | 94  | 172 | 130 |
| B | 305 | 173 | 306 | 151 | 463 | 189 | 203 | 39  | 115 | 111 | 112 | 85  |
| C | 145 | 95  | 200 | 157 | 219 | 283 | 185 | 25  | 152 | 148 | 166 | 182 |
| D | 318 | 600 | 448 | 697 | 606 | 735 | 149 | 61  | 188 | 282 | 236 | 480 |
| E | 143 | 88  | 174 | 115 | 195 | 161 | 246 | 26  | 181 | 72  | 151 | 92  |
| F | 123 | 129 | 143 | 124 | 157 | 146 | 50  | 16  | 80  | 42  | 76  | 67  |
| G | 200 | 370 | 248 | 445 | 247 | 720 | 185 | 193 | 185 | 459 | 175 | 576 |
| H | 388 | 49  | 744 | 53  | 474 | 104 | 498 | 26  | 640 | 171 | 719 | 215 |

TABLE 5

Concentration of solids in each formulation, milligrams per milliliter

|   | 1   | 2   | 3   | 4   | 5   | 6   | 7   | 8   | 9   | 10  | 11  | 12  |
|---|-----|-----|-----|-----|-----|-----|-----|-----|-----|-----|-----|-----|
| A | 4.1 | 3.5 | 5.3 | 4.8 | 5.4 | 4.7 | 2.9 | 3.7 | 4.0 | 1.8 | 4.6 | 2.0 |
| B | 2.7 | 1.8 | 3.7 | 1.4 | 4.6 | 1.5 | 1.9 | 0.5 | 2.2 | 0.9 | 2.1 | 0.8 |
| C | 3.5 | 3.0 | 4.9 | 2.8 | 5.2 | 4.4 | 3.0 | 2.6 | 3.9 | 2.9 | 4.6 | 2.9 |
| D | 1.6 | 2.8 | 2.3 | 3.1 | 3.8 | 2.8 | 0.9 | 1.2 | 1.3 | 1.5 | 2.0 | 2.4 |
| E | 3.5 | 3.2 | 4.7 | 3.9 | 4.9 | 4.1 | 3.0 | 2.1 | 3.9 | 2.1 | 4.3 | 2.4 |
| F | 3.0 | 2.7 | 3.2 | 2.7 | 4.0 | 2.8 | 0.7 | 1.1 | 1.9 | 0.2 | 2.1 | 1.5 |
| G | 4.0 | 3.7 | 5.4 | 4.5 | 5.2 | 5.1 | 2.7 | 3.4 | 3.9 | 3.2 | 4.3 | 3.7 |
| H | 1.9 | 0.3 | 3.7 | 0.3 | 2.7 | 0.6 | 1.5 | 0.4 | 2.9 | 1.1 | 4.3 | 1.0 |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

I claim:
1. A method of preparing nanoparticles comprising:
    (a) providing:
        (i) a first stock solution comprising an active agent and polymers admixed with one or more organic solvents;
        (ii) a second stock solution comprising a surfactant and a solvent in aqueous phase;
        (iii) a third stock solution comprising a water or buffer quench solution; and
        (iv) a fourth stock solution comprising an aqueous carrier and beta-cyclodextrin;

(b) combining a volume of said first stock solution and a volume of said second stock solution to form an emulsification solution;

(c) emulsifying said emulsification solution;

(d) combining the emulsion formed in step (c) with a volume of the third stock solution; and (e) adding a volume of the fourth stock solution to the solution formed in step (d); and separating beta-cyclodextrin and dissolved unencapsulated active agent from the resulting solution.

2. The method according to claim 1, wherein said active agent is selected from penicillins, aminopenicillins, penicillins in conjunction with penicillinase inhibitor and/or antifungal agents, cephalosporins, cephamycins, carbapenems, fluoroquinolones, tetracyclines, macrolides, aminoglycosides, erythromycin, bacitracin zinc, polymyxin, polymyxin B sulfates, neomycin, gentamycin, tobramycin, gramicidin, ciprofloxacin, trimethoprim, ofloxacin, levofloxacin, gatifloxacin, moxifloxacin, norfloxacin, sodium sulfacetamide, chloramphenicol, tetracycline, azithromycin, clarithyromycin, trimethoprim sulfate, bacitracin, cortico steroids, medrysone, prednisolone, prednisolone acetate, prednisolone sodium phosphate, fluormetholone, dexamethasone, dexamethasone sodium phosphate, betamethasone, fluoromethasone, antazoline, fluoromethalone acetate, rimexolone, loteprednol etabonate, diclofenac (diclofenac sodium), ketorolac, ketorolac tromethamine, hydrocortisone, bromfenac, flurbiprofen, antazoline, xylometazoline, cromolyn sodium, lodoxamide tromethamine, olopatadine HCl, nedocromil sodium, ketotifen fumarate, levocabastine HCL, azelastine HCL, pemirolast (pemirolast potassium), epinastine HCL, naphazoline HCL, emedastine, antazoline, pheniramine, sodium cromoglycate, N-acetyl-aspartyl glutamic acid, amlexanox,5-fluorouracil (5-FU), CPT- 11, 10-hydroxy- 7-ethylcamptothecin (SN38), S-I capecitabine, ftorafur, 5'deoxyflurouridine, UFT, eniluraciI, deoxycytidine, 5-azatyrosine, 5-azadeoxycytosine, allopurinol, 2-chloroadenosine, aminopterin, methylene-10-deazaaminopterin (MDAM), oxaplatin, picoplatin, tetraplatin, satraplatin, platinum-DACH, ormaplatin, [SP-4-3-(R)]-[1,1-cyclobutanediearboxylato-(2-)](2methyl-1,4-butanediamine-N,N')platinum (CI-973), and analogs thereof, 9-aminocamptothecin, 10,11-methylenedioxycamptothecin, karenitecin, 9-nitrocamptothecin, 6-[[2-(dimethylamino)ethyl]amino]-3-hydroxy-7H-indeno[2,1-c]quinolin-7-one dihydrochloride (TAS 103), L-phenylalanine mustard, ifosphamidemefosphamide, trophosphamide carmustine, epothilones A-E, tomudex, 6-mercaptopurine, 6-thioguanine, karenitecin, acyclovir, valacyclovir, ganciclovir, amantadine, rimantadine, lamivudine, zidovudine, bevacizumab, trastuzumab, rituximab, 20-epi-1α, 25dihydroxyvitamin D3, 4-ipomeanol, 5ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, antidorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, carbetimer, carboplatin, carboxamide-amino-triazole, carboxyamidotriazole, methylglyoxal maleimide, carmustine, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflomithine, eflomithine hydrochloride, elemene, elsarnitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, flurocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide ilomastat, imidazoacridones, imiquimod, immunostimulant peptides, insulin-like growth factor-1 receptor inhibitor, interferon agonists, interferon alpha-2A , interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, milteCosine, mirimostim, mismatched double stranded RNA, mitindomide, mitocarcin, mitocromin, mitogillin, mitoguazone, mitolactol, mitomalein, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2n, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinarnide, RNAi, rogletimide, rohitukine, romurtide, roquinimex, rubiginone B1, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride, siRNA or any combinations thereof.

* * * * *